US012751660B2

(12) United States Patent
Klinzing et al.

(10) Patent No.: US 12,751,660 B2
(45) Date of Patent: Oct. 6, 2026

(54) TREATMENT OF AN EPILEPSY-ASSOCIATED DISORDER

(71) Applicant: Eberhard Karls Universitaet Tuebingen Medizinische Fakultaet, Tuebingen (DE)

(72) Inventors: Jens Klinzing, Tuebingen (DE); Hong-Viet Victor Ngo, Hamburg (DE)

(73) Assignee: Eberhard Karls Universitaet Tuebingen Medizinische Fakultaet, Tuebingen (DE)

( * ) Notice: Subject to any disclaimer, the term of this patent is extended or adjusted under 35 U.S.C. 154(b) by 587 days.

(21) Appl. No.: 18/101,931

(22) Filed: Jan. 26, 2023

(65) Prior Publication Data

US 2023/0165510 A1 Jun. 1, 2023

Related U.S. Application Data

(63) Continuation of application No. PCT/EP2021/069843, filed on Jul. 15, 2021.

(51) Int. Cl.
*A61B 5/375* (2021.01)
*A61B 5/00* (2006.01)
(Continued)

(52) U.S. Cl.
CPC ............ *A61B 5/375* (2021.01); *A61B 5/4094* (2013.01); *A61B 5/24* (2021.01); *A61B 5/369* (2021.01); *A61B 5/41* (2013.01); *A61B 5/72* (2013.01)

(58) Field of Classification Search
CPC ......... A61B 5/375; A61B 5/4094; A61B 5/24; A61B 5/369; A61B 5/41; A61B 5/72; A61B 5/4812
See application file for complete search history.

(56) References Cited

U.S. PATENT DOCUMENTS 9,848,816 B1 12/2017 Bodner et al.
2009/0062676 A1* 3/2009 Kruglikov .............. A61B 5/378 600/544

(Continued)

FOREIGN PATENT DOCUMENTS

WO WO-2019033213 A1 * 2/2019 ......... A61N 1/36092
WO 2022023065 A1 2/2022

OTHER PUBLICATIONS

International Preliminary Report on Patentability (IPRP) for International Application No. PCT/EP2021/069843, issued Jan. 31, 2023 (9 pages).

(Continued)

*Primary Examiner* — Jennifer Robertson
*Assistant Examiner* — Jonathan Drew Moroneso

(57) ABSTRACT

The invention relates to an apparatus and a method for treating an epilepsy-associated disorder in a living being by acoustically modulating interictal epileptiform discharges (IEDs). The apparatus comprises an electrode set for obtaining an electroencephalogram, an audio output device, and an analysis and control unit configured to detect IEDs and to trigger delivery of an audio signal in temporal dependence on the detected event. In preferred embodiments, the audio signal comprises short bursts of 1/f noise administered with a defined delay, particularly between about one and three seconds after the negative peak of an IED, which has been found to reduce the rate and amplitude of subsequent epileptic discharges. The system is suitable for non-invasive use, including during NonREM sleep, and may improve symptoms associated with childhood epilepsy.

13 Claims, 8 Drawing Sheets

(51) Int. Cl.
*A61B 5/24* (2021.01)
*A61B 5/369* (2021.01)

(56) References Cited

U.S. PATENT DOCUMENTS

| | | | | |
|---|---|---|---|---|
| 2015/0313498 | A1* | 11/2015 | Coleman | A61B 5/38 600/383 |
| 2020/0163610 | A1* | 5/2020 | Osorio | A61N 1/36064 |
| 2021/0346096 | A1* | 11/2021 | He | A61B 5/37 |

OTHER PUBLICATIONS

Fattinger, et al. "Closed-Loop Acoustic Stimulation During Sleep in Children With Epilepsy: A Hypothesis-Driven Novel Approach to Interact With Spike-Wave Activity and Pilot Data Assessing Feasibility." Frontiers in Human Neuroscience, vol. 13, 166, May 21, 2019, pp. 1-10 (10 pages).

Extended European Search Report for EP Application No. EP20187984.8, dated Jan. 12, 2021 (9 pages).

International Search Report and Written Opinion of the International Searching Authority for PCT Application No. PCT/EP2021/069843, mailed Sep. 16, 2021 (17 pages).

* cited by examiner

TREATMENT OF AN EPILEPSY-ASSOCIATED DISORDER

CROSS-REFERENCES TO RELATED APPLICATIONS

This patent application is a continuation of copending international patent application PCT/EP2021/069843 filed on 15 Jul. 2021 and designating the U.S., which has been published in English, and claims priority from European patent application EP 20 187 984.8 filed on 27 Jul. 2020. The entire contents of these prior applications are incorporated herein by reference.

FIELD OF THE INVENTION

The present invention relates to an apparatus for the treatment of an epilepsy-associated disorder in a living being and to a method for the treatment of an epilepsy-associated disorder in a living being.

The present invention relates to the field of biosciences, in particular neurosciences.

BACKGROUND OF THE INVENTION

Epilepsy is a group of neurological disorders characterized by recurrent epileptic seizures. Epileptic seizures are episodes that can vary from brief and nearly undetectable periods to long periods of vigorous shaking. The underlying mechanism of epileptic seizures is excessive and abnormally synchronous neuronal activity in the cortex of the brain. The reason this occurs in most cases of epilepsy is unknown.

Rolandic epilepsy (RE; also benign epilepsy with centrotemporal spikes, BECTS) is the most common form of childhood epilepsy. RE is associated with a series of cognitive deficits, including impaired language, academic success, simultaneous information processing, as well as memory storage and retrieval. Overt seizures occur predominantly during the night and tend to be rare (1-2/year). However, electroencephalographic recordings show frequent interictal epileptiform discharges (IEDs) during quiet behavior and sleep. IEDs are most common during early NonREM (non-rapid eye movement) sleep and present in the EEG as sharp high-amplitude deflections or "spikes", sometimes followed by a slower surface negative wave. As indicated by its name BECTS, spikes are typically most prevalent over centro-temporal sites, with neocortical sources clustered around the central gyrus. However, their generation involves thalamocortical loops. IED intensity is correlated with the severity of cognitive impairments and their location is linked to the nature of the deficits.

IEDs can show parallels to physiological sleep oscillations in terms of involved brain areas and circuit mechanisms. These sleep rhythms include slow waves, spindles, sharp-wave ripples, which are considered essential for plastic processes related to memory consolidation as well as the homeostatic regulation of global synaptic strength. In Rolandic epilepsy, IEDs are most closely linked to sleep spindles, which are an important driver of memory formation and correlate with intelligence. Like IEDs, spindles are generated in thalamocortical networks, and might rely partly on the same neuronal microcircuits and cellular generation mechanisms. Indeed, IEDs interfering with spindles might be a cause for cognitive impairments in Rolandic epilepsy.

The occurrence of sleep spindles in thalamo-cortical networks is topdown regulated by the neocortical slow-oscillation (SO) with the depolarizing SO upstate driving GABA-ergic networks of the thalamic nucleus reticularis into spindle-rhythm generation. During the hyperpolarizing SO downstate, on the other hand, spindles are absent. Indeed, the SO represents an oscillatory mechanism that regulates excitability over widespread areas including not only the neocortex and thalamus, but also the hippocampus and brainstem structures. Importantly, SOs can be controlled in humans by external auditory stimulation. Presentation of a single auditory stimulus during sleep is known to elicit a SO-like wave, the so-called K-complex, that often comprises a spindle during its (surface positive) depolarizing phase.

Epilepsy is usually treated with daily medication once a second seizure has occurred, while medication may be started after the first seizure in those at high risk for subsequent seizures. Common epilepsy drugs, such as Ospolot (Sultiame), Keppra (Leventiracetam), or Trileptal (Oxcarbazepin), interact with the brain chemistry of the patients and may have severe side effects, such as stomach problems, loss of appetite, loss of weight, headache, dizziness, anxiety states, hallucinations, apathy etc.

Other experimental therapies are based on the interruption of ongoing epileptic brain activity through electrical or magnetic stimulation. These approaches also intervene massively in physiological brain activity and their use is not realistic over a longer period of time and outside of a clinical setting.

Fattinger et al. (2019), Closed-Loop Acoustic Stimulation During Sleep in Children With Epilepsy: A Hypothesis-Driven Novel Approach to Interact With Spike-Wave Activity and Pilot Data Assessing Feasibility, Frontiers in Human Neuroscience, 13 (May), 1-10, have examined the potential effect of auditory stimulation on IEDs in children with epilepsy. In this study, auditory stimuli were presented timed-locked to the up or down phases of slow waves in children with heterogeneous epilepsy subtypes. Overall there was no effect of stimulation on the rate of IEDs.

Hu et al. (2020), The Effect of External Voltage Stimulation on Absence Seizures, Technol. Health Care, 28, 245-251, describe the electromagnetic interference with epileptic activity. However, such method is highly invasive and not practicable for a longer treatment outside of a clinical context.

Min et al. (2011), Focused Ultrasound-Mediated Suppression of Chemically-Induced Acute Epileptic EEG Activity, Epilepsy Curr.; 11(6): 196-197, describe the use of ultrasound for the suppression of epileptic activity. However, such method did not prove helpful in practice.

SUMMARY OF THE INVENTION

Against this background, it is an objective underlying the invention to provide an apparatus and method for the treatment of an epilepsy-associated disorder by means of which the problems of the current therapies or approaches are avoided or at least reduced. In particular an apparatus and method should be provided which are less invasive while, at the same time, significantly reduce epilepsy-associated disorders.

The present invention satisfies these and other needs.

This objective is met by an apparatus for the treatment of an epilepsy-associated disorder in a living being, comprising, in an operatively linked manner:

- an electrode set capable of obtaining an electroencephalogram (EEG) of a living being;
- an audio output device capable of delivering an audio signal to the living being;

an analysis and control unit capable of:
(i) detecting interictal epileptic discharges (IED) in the EEG of the living being, and
(ii) causing the audio output device to deliver the audio signal in time dependence of a detected IED.

This objective is also met by a method for the treatment of an epilepsy-associated disorder in a living being, comprising the following steps:
(1) obtaining an electroencephalogram (EEG) of a living being;
(2) detecting interictal epileptiform discharges (IED) in the EEG of the living being, and
(3) administering an audio signal to the living being in time dependence of a detected IED.

The inventors have realized that the administration of an audio signal to a living being suffering or suspected of suffering from epilepsy in time dependence of a detected IED can significantly reduce the rate and amplitude of epileptic discharges or IEDs and, thus, symptoms or consequences of epilepsy-associated disorders.

According to the invention an "epilepsy-associated disorder" refers to any neurological disturbance or deficit characterized by or being the result of epileptic seizures or discharges in the brain. Such disorder includes, without being limited thereto, epilepsy, childhood epilepsy, Rolando epilepsy, benign epilepsy with centro-temporal spikes (BECTS). It also includes developmental disorders associated with epilepsy, cognitive deficits, including impaired language, academic success, simultaneous information processing, as well as memory storage and retrieval.

A "living being" refers to any organism, including animal and human being, in particular a human being, preferably a child, suffering or being suspected of suffering from an epilepsy-associated disorder.

An "interictal epileptiform discharge (IED)" refers to anomalies in electroencephalograms (EEG) which consist of spike waves and sharp waves, and are characteristic signatures of epilepsy. A single IED, also referred to as an 'epileptic spike', in an EEG, is composed of a negative peak (downward curve) followed by a subsequent positive peak (upward curve). Both peaks are typically observed with a time delay of ≤0.1 seconds.

According to the invention, an "electrode set" refers to any electrode or plurality of electrodes capable of obtaining an electroencephalogram (EEG). Such electrodes are also referred to as 'EEG electrodes' or 'polysomnographic electrodes'. In an embodiment of the invention the electrode set includes at least one detection electrode configured for obtaining an EEG in proximity to an epileptic focus, and a reference electrode. The latter is, in another preferred embodiment, configured for obtaining a reference signal at the *Processus mastoideus.*

According to the invention, the "audio output device" refers to any apparatus capable of delivering an audio signal to a living being, in particular to the hearing organ(s) or ear(s) of the individual. Such device incudes, without being limited thereto, a speaker, earphone, headphones, etc.

According to the invention, an "audio signal" refers to a sound perceivable or hearable by the living being via the hearing organs or ears of the individual. It includes, without being limited thereto, a tone, such as a sinus tone, sound, noise, in particular a 1/f noise. The audio signal can be of any length and volume appropriate for the intended purpose.

According to the invention, an "analysis and control unit" refers to any device capable of detecting interictal epileptic discharges (IED) in the EEG of a living being, and causing an audio output device to deliver an audio signal to the living being in time dependence of a detected IED. Typically, in an embodiment the 'analysis and control unit' is a soft- and hardware-based device comprising a processor and a computer readable storage medium. The computer-readable storage medium contains instructions for execution by the processor. The 'analysis and control unit', in an embodiment of the invention, is configured to record the activity of the electrode set, preferably of the detection electrode, e.g. by means of an EEG amplifier, such as a Digitimer D360 EEG amplifier. In an embodiment, the 'analysis and control unit' is configured to filter and sample the signal of the detection electrode, e.g. by a data acquisition interface, such as a CED Power1401 MK2 data acquisition interface. In an embodiment of the invention, the 'analysis and control unit' is configured to execute a software program using a threshold procedure to identify an IED in the EEG. In another embodiment, the software, when detecting an IED, triggers the delivery of the audio signal to the living being via the audio output device.

According to the invention, "in time dependence of a detected IED" means that the audio signal is delivered/administered to the living being temporarily linked to the occurrence on an IED. For instance, the audio signal is delivered/applied to the living being following an IED by a well-defined time delay, such as 0.01. 0.02, 0.03, 0.04, 0.05, 0.1, 0.2, 0.3, 0.4, 0.5, 1.0, 1.1, 1.2, 1.3, 1.4, 1.5, 2.0, 2.1, 2.2, 2.3, 2.4, 2.5, 3.0, 3.1, 3.2, 3.3, 3.4, 3.5, 4.0, 5.0, 6.0 etc. seconds after the occurrence of an IED, e.g. with reference to the negative peak of the IED. Timing may be restarted in case another IED is detected within the delay.

According to the invention, the elements of the apparatus are "operatively linked" which means that said elements are connected to each other, e.g. via cables, wires, lines or wirelessly, preferably to allow the automated delivery of an audio signal to the living being in time dependence of a detected IED.

The apparatus according to the invention can be designed as a mobile system allowing a facilitated use in daily practice.

Due to their less invasive nature the apparatus and method according to the invention have the potential to significantly improve the quality of the patients' lives.

All the features, embodiments, advantages and characteristics of the apparatus according to the invention also apply to the method according to the invention.

In an embodiment of the apparatus according to the invention the analysis and control unit is configured to cause the audio output device to deliver the audio signal to the living being at a time delay after a detected IED.

In an embodiment of the method according to the invention the audio signal is administered to the living being at a time delay after a detected IED.

This measure has the advantage that, according to the findings of the inventors, the rate of epileptic discharges or IEDs can be effectively reduced by applying or delivering the audio signal to the living being not directly during a discharge event or IED, respectively, but delayed in time with respect to the latter.

In another embodiment of the invention the time delay is between approx. 1 to 3 seconds relative to the negative peak of the detected IED.

The inventors have realized that the most efficient reduction of the rate of epileptic discharges or IEDs can be achieved when the audio signal is applied or delivered to the living being with a time delay of approx. 1 to 3 seconds relative to the negative peak of the detected IED. This measure has the advantage that it is not necessary to precisely determine the point in time of an epileptic discharge or IED or its separation into the negative and positive peaks, respectively. Approx. 1 to 3 seconds, in an embodiment of the invention, includes time delays of 0.7, 0.8, 0.9 and 3.1, 3.2, 3.3 seconds. Further, the indicated time span includes all time values in between these two limiting values, e.g. 1.1, 1.2, 1.3, 1.4, 1.5, 2.0, 2.1, 2.2, 2.3, 2.4, 2.5 seconds, etc.

In an embodiment of the invention the audio signal comprises 1/f noise.

The inventors have realized that such kind of audio signal is well-suited to suppress epileptic discharges or IEDs in the living being. According to the invention "1/f noise", also called 'pink noise', is a signal or process with a frequency spectrum such that the power spectral density (energy or power per frequency interval) is inversely proportional to the frequency of the signal. In pink noise, each octave (halving or doubling in frequency) carries an equal amount of noise energy.

In an embodiment of the invention, the analysis and control unit is configured to cause the audio output device to deliver the audio signal to the living being for a time period of approx. 50 ms, preferably with a volume of approx. 12 dB above the individual hearing threshold of the living being.

The inventors have realized that by delivering or applying the audio signal for the indicated period of time and volume particularly good results can be obtained by the apparatus according to the invention.

The individual hearing threshold can be determined by methods well-known in the art. For children under the age of 18 the hearing threshold is typically in the range of 43±3 dB.

In another embodiment of the invention the analysis and control unit comprises a band-pass filter for detecting the IED in the EEG of the living being, preferably a band-pass filter comprising frequency limits of approx. 20 and approx. 150 Hz.

This measure allows the isolation of the frequencies in the obtained EEG signal, which comprise the epileptic discharges or IEDs.

In another embodiment of the invention, the analysis and control unit is configured to run a threshold method using an amplitude threshold for detecting the IED.

This measure has the advantage that such a method is used which, according to the finding of the inventors, is particularly suited to detect an epileptic discharge or IED in the EEG.

In another embodiment of the invention, the electrode set comprises a detection electrode and/or a reference electrode.

This measure creates the constructive prerequisites for implementation of an appropriate electrode set. The EEG signal is recorded by the detection electrode and referenced against the reference electrode. It goes without saying that similar electrode sets achieve equivalent results.

In another embodiment of the invention, the analysis and control unit is further capable of:

(iii) determining the sleep phase of the living being, in particular the non-rapid eye movement (NonREM) sleep phase;

preferably the analysis and control unit is also capable of:

(ia) detecting IEDs in the EEG of the living being during a NonREM sleep phase, and (iia) causing the audio output device to deliver the audio signal in time dependence of a detected IED during the NonREM sleep phase.

This measure has the advantage that the apparatus is optimized for the detection of IEDs. This is because IEDs can be observed not only in the months between the seizures of a patient or in resting phases but in particular during the NonREM sleep phase. By looking that the living being is in the NonREM sleep phase before stimulating, on the one hand one increases the probability that the detected event is actually an IED, and not, for example, the chewing muscle activity of an awake being, and on the other hand one would not like to disturb a patient who is just falling asleep with tones and thus prevent healthy sleep. The inventors also assume that stimulation while awake has only a minor or even no effect on the IEDs. Further, no IEDs occur during REM sleep. The improved apparatus is, therefore, capable, to precisely detect the IED in the NonREM sleep phase and, as a consequence, to administer the audio signal at the right time.

The capability of the analysis and control unit to determine the sleep phase, in an embodiment of the invention, can be realized via the electrode set and/or (an) electrode(s) in addition to the detection and/or reference electrode.

In an embodiment of the invention, the audio output device is a headphone or earphone, preferably a bone conduction headphone or earphone.

This measure has the advantage that the audio output device is optimized for practical use. Headphones, in particular bone conduction headphones ensure a proper auditory stimulation of the living being without disturbing others being in the same room.

In another embodiment of the invention, the living being is or is suspected from suffering from epilepsy, preferably childhood epilepsy, further preferably Rolandic epilepsy.

This measure has the advantage that the apparatus according to the invention is adapted to the important variants of epilepsy for which effective non-invasive therapies do not exist so far.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention. The features mentioned in the specific embodiments are features of the invention and may be seen as general features which are not applicable in the specific embodiment but also in an isolated manner in the context of any embodiment of the invention.

The invention is now further described and explained in further detail by referring to the following non-limiting examples and figures.

EXAMPLES

1. Embodiment of the Apparatus

Figure 1:
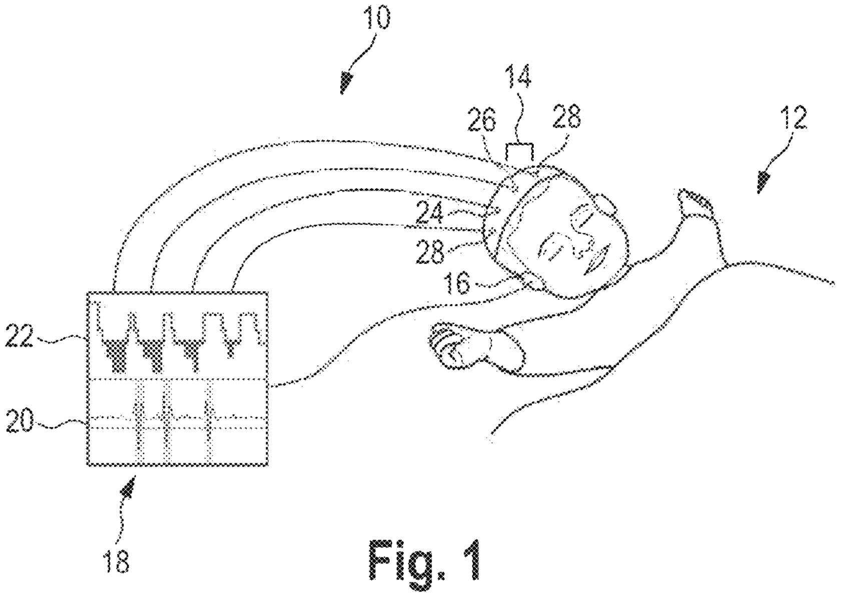
FIG. 1 Schematic illustration of an embodiment of the apparatus according to the invention.

In FIG. 1 a schematic illustration of an embodiment of the apparatus according to the invention is depicted, said apparatus is shown under the reference sign 10. The treated living being or child has the reference sign 12. The apparatus 10 comprises an electrode set 14 attached to the head of the child 12. The child 12 wears headphones 16 and, in the illustrated embodiment, is in a sleeping state. The electrode set 14 and the headphones 16 are connected via cables with an analysis and control unit 18. The analysis and control unit 18 is capable of detecting interictal epileptic discharges (IEDs 20, marked by grey vertical bars) in the EEG 22 (oscillating line; vertical straight line shows detection threshold) of the child 12. The analysis and control unit 18 is delivering an audio signal in time dependence of a detected IED 20 to the child 12 via the audio output device 16.

The electrode set 14, in the illustrated embodiment, comprises a detection electrode 24, a reference electrode 26, and, optimally, additional electrodes 28 for a better determination of the sleep phase of the child 12.

2. Introduction

In the illustrated study the inventors aimed at lowering IED rates during sleep in children with Rolandic epilepsy using auditory stimulation. The short tone bursts presented during sleep were expected to suppress spikes either by the immediate induction of a SO-like down-state or by inducing up-state related thalamic spindles interfering with thalamocortical IEDs generation. To explore these hypotheses, the inventors compared the effects of auditory stimulation between different conditions with the tone presented either immediately upon detection of a spike (“Negative peak” condition), 90 ms later (“Positive peak”), 500 ms later (“0.5 s delay”), or in a random delay interval 1-3 s following the negative peak of the spike (Random delay”). Effects on spike rates were compared with a sham control condition, and the inventors also compared the effects of sham and random stimulation in patients with those in healthy age-matched controls.

3. Material and Methods

Participants

A total of 14 subjects (7 females, 7 males; mean age±SD: 9.97±1.52; range: 6.60-11.76 years) participated in the study. Half of the participants ("patients") had previously been diagnosed with Rolandic epilepsy, benign epilepsy with centro-temporal spikes (BECTS), or BECTS-typical centro-temporal spikes, and did not show any known structural neuronal abnormalities. The other participants ("controls") had not been diagnosed with epilepsy or any other known neural disorders. Controls were matched to the patients by age (patients: 9.86±1.65 years; controls: 10.08±1.50 years; p=0.798) because the investigated form of epilepsy as well as physiological sleep characteristics change substantially with age. Four of the patients were on epilepsy medication. See Table 1 for further details. Two additional participants were excluded from analysis due to technical problems during the experimental night. Further four subjects were excluded who had previously presented with BECTS-typical centro-temporal spikes but showed no or almost no epileptic activity during the experimental night.

TABLE 1

Participant details.

| | Subject | Sex | Age | Detection electrode | Medication |
|---|---|---|---|---|---|
| Patients | 1 | m | 9.3 | T4 | Oxcarbazepin (2 × 450 mg) |
| | 2 | w | 10.8 | T4 | Levetiracetam (2 × 500 mg) |
| | 3 | w | 10.5 | T3 | |
| | 4 | m | 6.6 | Cz | |
| | 5 | m | 11.8 | T4 | Ospolot (2 × 50 mg) |
| | 6 | w | 9.6 | C3 | Ospolot (2 × 50 mg) |
| | 7 | w | 10.5 | C3 | |
| Controls | 8 | m | 6.9 | C3 | |
| | 9 | m | 9.6 | C3 | |
| | 10 | m | 10.9 | Cz | |
| | 11 | w | 10.8 | C3 | |
| | 12 | m | 11.4 | F4 | |
| | 13 | w | 10.2 | Cz | |
| | 14 | w | 10.8 | Cz | |

Participants in both groups were matched by age (no difference between groups, p=0.798). The detection electrode was chosen based on previously determined epileptic focus and spike amplitude in the recording night. Medication dose in Table 1 is given per day.

Table 2: Potential patients were preselected, approached, and informed about the study by an experienced pediatrician (S.R.) with access to the candidate's medical history. Potential control participants were contacted via the institute's volunteer database. Exclusion criteria were other neurological or psychological disorders, irregular sleeping patterns, or ongoing participation in other studies. The participants' parents gave their written informed consent, subjects gave their verbal consent, and both were free to abort the study at any stage. The study was approved by the local ethics committee of the Medical Faculty of the University Tubingen.

TABLE 2

Sleep parameters.

| | Subject # | S1 | S2 | S3 | S4 | REM | TST |
|---|---|---|---|---|---|---|---|
| Patients | 1 | 15.0 | 204.0 | 178.5 | 60.5 | 40.5 | 505.0 |
| | 2 | 68.0 | 390.0 | 66.0 | 20.0 | 95.0 | 643.0 |
| | 3 | 37.0 | 214.0 | 126.0 | 76.0 | 87.5 | 572.0 |
| | 4 | 1.5 | 47.5 | 461.0 | 98.5 | 16.0 | 639.0 |
| | 5* | 24.0 | 103.5 | 28.5 | 57.0 | 27.0 | 250.5 |
| | 6 | 20.0 | 162.5 | 254.0 | 53.5 | 0.0 | 496.0 |
| | 7 | 23.5 | 259.0 | 112.5 | 57.0 | 95.0 | 553.5 |
| Mean | | 27.50 ± 9.37 | 212.83 ± 46.00 | 199.67 ± 58.48 | 60.92 ± 10.62 | 55.6 ± 17.33 | 568.08 ± 25.85 |
| Controls | 8 | 15.0 | 151.0 | 128.0 | 40 | 69.0 | 404.0 |
| | 9 | 59.0 | 220.0 | 77.0 | 65.5 | 89.5 | 526.0 |
| | 10 | 51.0 | 267.5 | 94.0 | 70.5 | 93.0 | 631.5 |
| | 11 | 8.5 | 155.0 | 184.0 | 101.5 | 96.5 | 569.5 |
| | 12 | 65.0 | 151.0 | 144.5 | 55.0 | 50.5 | 583.0 |
| | 13 | 31.5 | 135.0 | 89.5 | 69.0 | 25.5 | 419.0 |
| | 14 | 26.5 | 280.5 | 69.5 | 63.5 | 78.5 | 553.5 |
| Mean | | 36.34 ± 8.31 | 194.29 ± 23.02 | 112.36 ± 15.70 | 66.43 ± 7.06 | 71.79 ± 9.79 | 526.64 ± 32.13 |

Time spent in each sleep stage (in min). There were no differences between groups in any sleep stage (independent t-tests, all p<0.15 uncorrected, subject 5 excluded from means and statistics). *For participant 5, polysomnographic recordings were only available for the first half of the night. Because the patient had difficulties falling asleep after a bathroom break the EEG was removed; the patient's mother reported normal sleep in the second half of the night.

Experimental Procedure

Accompanied by one parent, participants arrived at the laboratory at around 7:00 pm. EEG and other polysomnographic electrodes were attached, earphones were put on, the individual hearing threshold was determined (43.00±2.13 dB sound pressure level, mean±SEM), and sleepiness was rated verbally on the Stanford Sleepiness Scale. At around 10:00 pm, participants went to bed. Parents either slept in the same room as the child or in a room next door. Acoustic stimulation was started as soon as the polysomnography indicated reliable sleep patterns and continued for about 3 h (174.14±13.94 min, mean±SEM). Depending on the participant's sleep pattern and frequency of detectable spikes, this resulted in 183.19±18.48 stimulations per subject and condition (see below). After the stimulation period, participants continued sleeping without further interventions.

Electrophysiological Recordings

Throughout the night, the inventors acquired electroencephalographic recordings at 19 electrode sites (Fp1, Fp2, F3, Fz, F4, F7, F8, C3, Cz, C4, T3, T4, T5, T6, P3, Pz, P4, O1, and O2, according to the International 10-20 system), referenced to the mastoids (averaged M1, M2). Additionally, the inventors obtained bipolar electromyographic recordings from the chin as well as horizontal and vertical electrooculography to aid sleep scoring. Data were recorded and amplified with a Brain Products recording system (Brain Products GmbH, Gilching, Germany) at a sampling frequency of 500 Hz and processed using Matlab 2017a (Mathworks, Natick, USA), Fieldtrip (fieldtriptoolbox.org), Python 3.7, Seaborn 0.9.0 (seaborn.pydata.org). In most cases, analysis was restricted to the Cz electrode site as well as the individual detection electrode (DET) nearest to the focus of the patient's spike activity. For control subjects, the same electrode as the age-matched patient was chosen as detection electrode.

Auditory Stimulation

The EEG electrode closest to the known epileptic focus was used to detect epileptic spikes. The signal from this detection electrode (DET) was passed on to the stimulation setup, referenced to the EEG system's mastoid electrodes. In cases in which recordings showed higher spike amplitudes at another electrode, the detection electrode was switched before starting the stimulation. Activity at the detection electrode was recorded by a Digitimer D360 EEG amplifier (Digitimer Ltd., Welwyn Garden City, UK), using the same reference as the EEG system. The signal was real time-filtered between 4 and 150 Hz. The DET signal was sampled at 200 Hz by a CED Power1401 MK2 data acquisition interface (Cambridge Electronic Design, Cambridge, UK). Spike detection was performed via a custom-made script running under Spike2 7 (Cambridge Electronic Design, Cambridge, UK) using a threshold procedure. The script triggered acoustic stimulation by short bursts of pink noise (50 ms duration, +12 dB above previously established hearing threshold), which were administered using in-ear headphones. Detection threshold and frequency range for the online filtering were continuously adapted to maximize spike detections (true positives) while minimizing false detections of other events (false positives).

Figure 2:
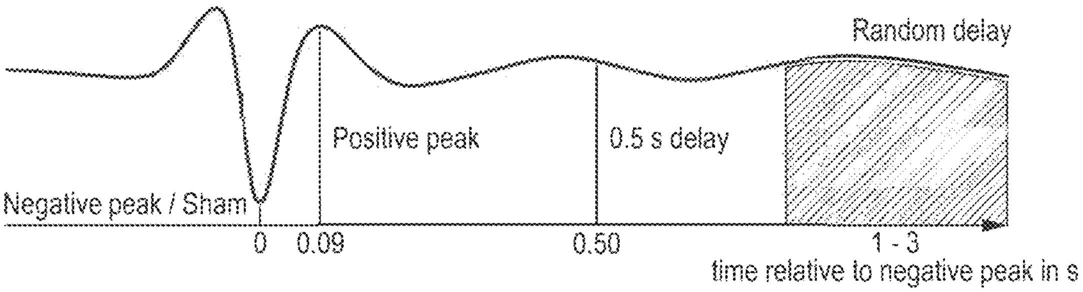
FIG. 2 Stimulation protocol. In a study assessing the efficacy of the invention, epileptic spikes (IEDs) were detected using an amplitude threshold. Auditory stimulation was performed either at the time of an IED's negative peak ("Negative peak" condition), its positive peak (approximated by introducing a stimulation delay of 90 ms, "Positive peak" condition), 0.5 s after the negative peak ("0.5 s delay" condition), or at a random delay between 1 and 3 s after the negative peak ("Random delay" condition). In a "Sham" control condition, no stimulus was delivered upon a detected IED. In a healthy control group, only the Random delay and Sham conditions were executed. Stimulation time points were selected randomly during NonREM sleep and with the same temporal structure as in the patient group. The stimulation conditions were conducted in blocks of 30 s.

The inventors performed auditory stimulation during Non-REM sleep (stages 2, 3, and 4) in five conditions, randomly selected for blocks of 30 s (FIG. 2). Tones were presented either at the time of the negative peak of a detected spike ("Negative peak"), or 90 ms later during its subsequent positive peak ("Positive peak"), or 0.5 s after the negative peak ("0.5 s delay" condition), or with a random delay between 1 and 3 s after the negative peak ("Random delay"). In a "Sham" control condition, the negative peak of a spike was detected but no auditory stimulation was performed. Stimulation was paused at signs for arousal, awakening, or REM sleep.

Data Analyses

Figure 3:
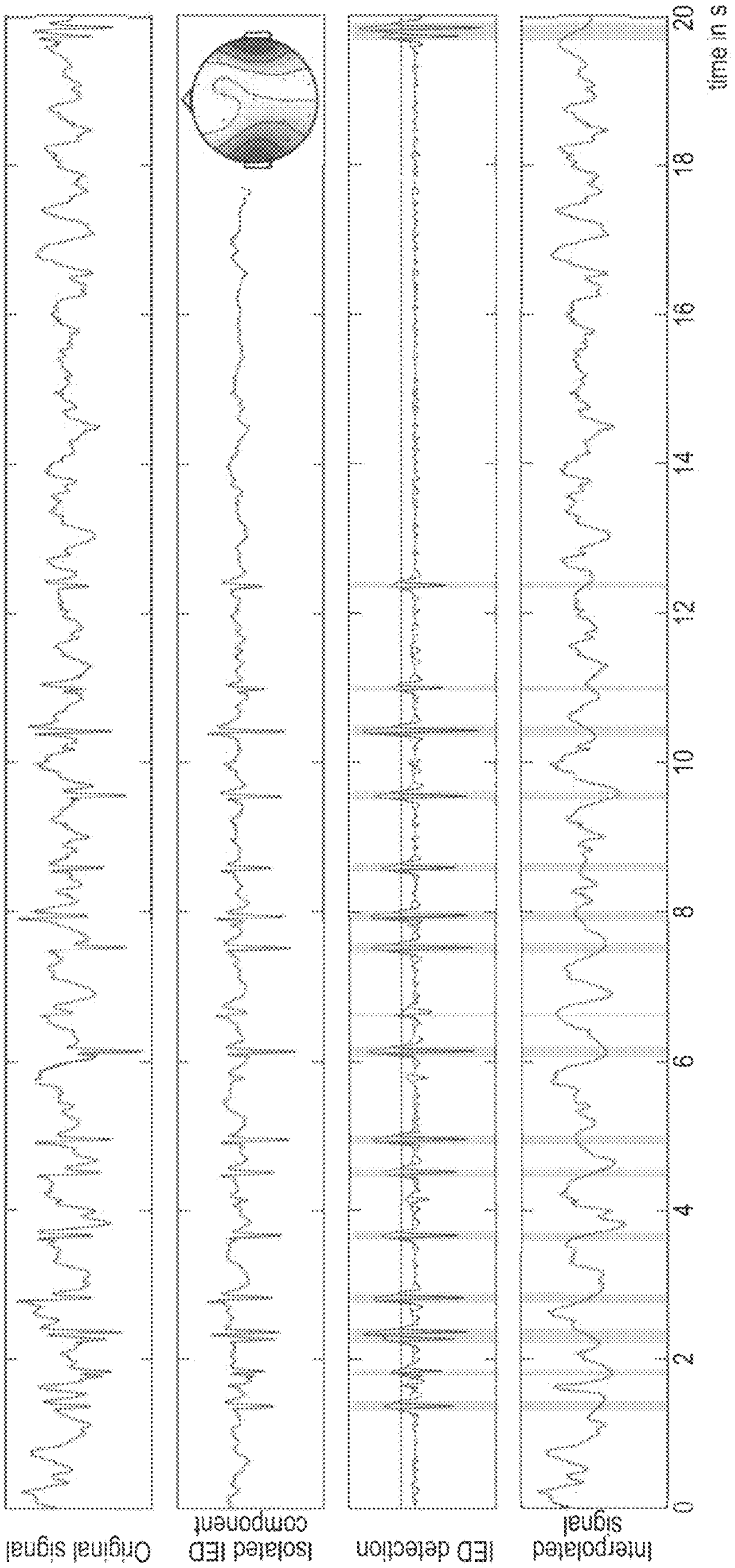
FIG. 3 Spike detection and EEG signal interpolation. From the original timeseries data (first trace from top) the inventors extracted components showing prominent IEDs (second trace, head plot shows highly localized spike topography). After highpass-filtering, a threshold (straight horizontal line) was determined and used to detect spikes (third trace). Detected IEDs were removed and the EEG signal was interpolated, resulting in an IED-free signal (fourth trace). Vertical grey bars indicate the detected IED events.

IED detection and removal by EEG signal interpolation. The inventors detected interictal epileptiform discharges automatically using custom-made algorithms. The inventors first performed an Independent Component Analysis (ICA) decomposition (fastICA) and manually selected ICA components that did not contain IED-like waveforms for rejection. After a back-projection into EEG space, the inventors highpass-filtered the EEG signal of the detection electrode at 5 Hz, extracted the envelope using a Hilbert transform, and smoothed the envelope with a moving average of 50 ms length. For each subject, the inventors determined the detection threshold as the mean+2.5 times the standard deviation (SD) of the envelope signal over all NonREM periods. For one subject, the scaling factor was adjusted to 2.0. An IED was registered whenever the enveloped exceeded the threshold for more than 10 and less than 500 ms. Putative events following within <50 ms were merged. For each IED event, the inventors marked on- and offset where the envelope crossed the threshold. The inventors then calculated the IED rate, i.e. events per minute, separately for each experimental condition. To assess differences in IED rate between condition, the inventors pooled IED rates for all 30-s stimulation blocks across patients and then performed an Analysis of Variance (ANOVA) with a fixed Factor 'Condition' (Negative peak/Positive peak/0.5 s delay/Random delay/Sham) and IED rate as the dependent variable. Post-hoc t-tests were subjected to Holm correction for multiple comparisons. To remove confounding effects of IEDs in subsequent analyses, the inventors created an IED-free dataset by performing a spline interpolation on the EEG time-domain signal for each identified IED with additional padding of 100 ms on each side (FIG. 3).

Spectral analysis. To assess spectral power (for patients on the interpolated signal), the inventors segmented data for each experimental condition into epochs of 4.096 s with an overlap of 50%. The inventors estimated the frequency content of the signal using the irregular-resampling auto-spectral analysis (IRASA) approach. This procedure allows the isolation of oscillatory spectral components from fractal 1/f background component typical for electrophysiological recordings. The inventors expressed the magnitude of the oscillatory component relative to the fractal component. Power was assessed by averaging the resulting values for the slow wave (0.5-4 Hz), theta (4-8 Hz) and spindle (10-18 Hz) bands, respectively. Peak spindle frequencies were determined individually for each subject. The inventors assessed statistical differences in theta and spindle power as well as spindle peak frequencies by performing a repeated measures ANOVA with between-subject factor 'Group' (Patients/Controls) and within-subject factors 'Electrode' (Cz/DET) and 'Condition' (Random delay/Sham).

Offline detection of SOs and sleep spindles. Discrete slow oscillation and spindle events were detected during NonREM epochs across the entire night. For SOs, each EEG channel was first bandpass-filtered from 0.3 to 1.25 Hz. Then positive to negative zero crossings were identified and all intervals between consecutive zero crossings shorter than 0.8 or longer than 2 s (corresponding to frequencies of 0.5-1.25 Hz in the SO range) were discarded. Across the remaining intervals the negative peaks and the amplitude from negative to the positive peak were averaged. The resulting mean values were multiplied by 1.5 and served as detection threshold, i.e. intervals were labelled as a SO whenever its negative peak was lower than 1.5 times the mean negative peak value and the amplitude exceed the 1.5 times the mean amplitude threshold. To detect sleep spindles, the inventors bandpass-filtered the EEG data between 10 and 18 Hz and derived the root-mean-square (RMS) of the signal with a 200-ms sliding window, followed by smoothing with an identical window length. The inventors determined a detection threshold from the mean RMS signal across all NonREM epochs+1.5 times its SD. Based on this threshold, intervals for which the RMS signal exceeded the threshold for more than 0.4 s and less than 3 s were labelled as discrete spindle events. The inventors determined SO and spindle rate, i.e., the number of detected events per minute, separately for each experimental condition. Statistical assessment of SO and spindle density was based on a repeated measures ANOVA with the between-subject factor 'Group' (Patients/Controls) and the within-subject factors 'Electrode' (Cz/DET) and 'Condition' (Random delay/Sham). The inventors further examined how sleep spindles relate to IEDs by estimating the rate, i.e. events per minutes, of detected spindles and spindle power (10-16 Hz) for all 30-s stimulation blocks. The inventors correlated spindle rates and IED rates (for the same blocks) across all patients.

Analysis of evoked responses. For analyses of IED-related and stimulation-related activity, non-interpolated data were cut into segments of 14 s around detected spikes. Segments containing artifacts were rejected using a semi-automatic procedure (identification of candidate artifacts by thresholding the z-transformed signal, followed by thorough visual inspection). Data were highpass-filtered at 0.1 Hz and notch-filtered between 45 and 55 Hz (Butterworth filter). Evoked potentials were corrected by subtracting an average baseline value between −1.5 and −0.5 s before the detected spike. For time-frequency analyses 12-cycle Morlet wavelets were applied and visualized as power change relative to the average power at that frequency between −1.5 and −0.5 s.

Statistical analyses for evoked potentials and evoked time-frequency response relied on non-parametric cluster-permutation statistics to control inflation of type I errors due to multiple comparisons. For time-frequency data, samples were selected that showed significant differences in power in relation to the respective contrast condition (two-tailed paired-samples t-tests, sample-level alpha=0.05). In the resulting statistical map, adjacent samples were grouped into positive and negative clusters for which cluster-level statistics were calculated by summing up the t-values within each cluster. These were tested against a reference distribution (cluster-level alpha=0.05), generated by shuffling the association of data and condition (10,000 permutations) and, for each permutation, taking the maximum statistics among all clusters.

In a separate step, the inventors isolated evoked spindle power by averaging time-frequency data over all samples within a spectral-temporal segment after applying a broad Tukey window ($\alpha$=0.25) to attenuate power at the edges. The analyzed segment corresponded to power occurring in the 10-18 Hz spindle band and 0.4-1.2 s following spike onset (negative peak). The spectral and temporal width of the window was determined based on the grand average over all control subjects for the Cz electrode. The inventors statistically assessed evoked spindle power by performing a repeated measures ANOVA with factors 'Electrode' (Cz/DET) and 'Condition'. Results were Greenhouse-Geisser-corrected if the assumption of sphericity was violated. Effect sizes ($n^2$ for ANOVA, Cohen's d for post hoc tests) are provided for significant tests.

4. Results

Acoustic Stimulation Reduced Interictal Epileptic Discharges

To assess the effect of auditory stimulation on the occurrence of IEDs, the inventors automatically identified discrete IED events and examined the spike rate across the different stimulation conditions. IED rate was determined for each stimulation block and pooled across all patients. This analysis revealed a striking reduction in IEDs driven by a reduction in the Random delay condition (23.319±0.682 events/min) in comparison to the Sham condition (26.452±0.764 events/min) corresponding to a decrease of ~11% (F(4,1328)=2.615 and p=0.034, $\eta$2=0.008, with Holm corrected p=0.015 for Random delay vs. Sham post-hoc test).

Patients with Rolandic Epilepsy Express Slower Sleep Spindles

In light of the distinct effect of Random stimulation decreasing spike rate in comparisons with the Sham control condition, in subsequent analyses the inventors aimed to clarify the mediating mechanism of this effect. Specifically, the inventors wondered whether this effect is linked to alterations in slow wave and spindle activity, or might be a consequence of generally lightened sleep during random stimulation. To this end, as a first step, the inventors compared physiological oscillations between the conditions and between patient and control groups using IRASA-based spectral power analyses of the EEG signal.

Figure 4:
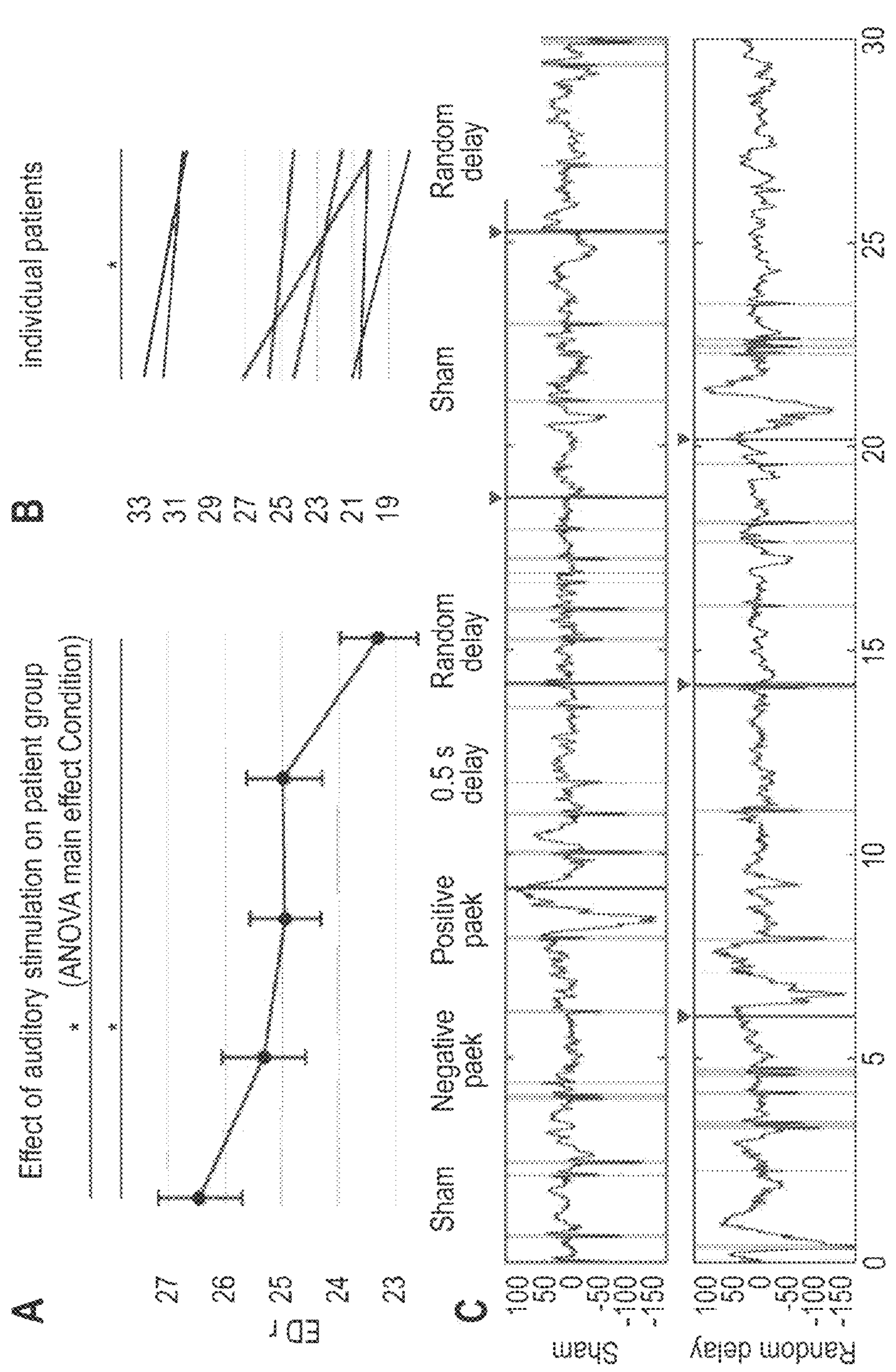
FIG. 4 Acoustic random-delay stimulation suppressed IEDs in all patients. A) IED density was modulated by the stimulation (ANOVA on pooled data, $p=0.034$) and significantly lower in the Random delay condition compared to Sham ($p=0.015$, Holm corrected). B) IEDs were suppressed in each of the seven patients (paired t-test on individual data, $p=0.020$). C) Representative examples for 30-s blocks without stimulation (Sham, 26 detected IEDs) and Random delay stimulation (Random delay, 18 detected IEDs). Triangles over dark lines show sham and random delay stimulations, respectively. Grey bars mark detected IEDs. Note that the second stimulation in the Random delay condition (at around t=14 s) by chance occurred close to another IED. These coincidences present a negative bias, suggesting that the results underestimate the actual effect of the stimulation. $^{*}p<0.05$.
Figure 5:
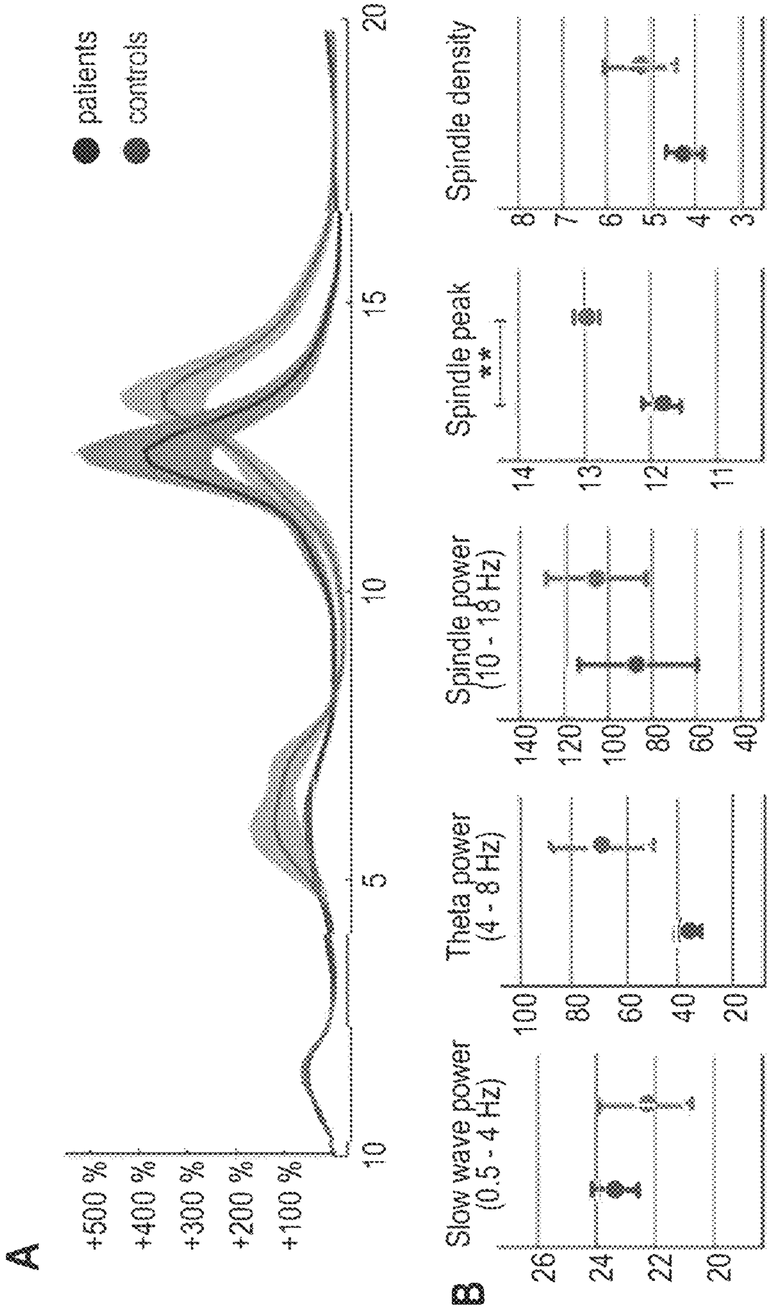
FIG. 5 Rolandic epilepsy is associated with slower sleep spindles. Results of analysis of IRASA-derived power estimates and spindle detection. (A) Oscillatory component of IRASA power spectra relative to fractal 1/f component. Note clear peaks in the spectrum for slow wave, theta, and spindle frequency bands. (B) Comparison of slow wave power, theta power, spindle power, spindle peak frequency, and spindle rate between patients and controls. Sleep spindles reached their peak power at a lower frequency in patients than in controls ($p=0.002$). All data shown as mean±SEM for sham condition and electrode Cz. $^{**}p<0.01$.

An overall examination of spectral power in Sham and Random delay conditions revealed distinct peaks in the 0.5-4 Hz slow wave, 4-8 Hz theta, and 10-18 Hz spindle bands in both groups (FIG. 5A). Testing across groups (Patient/Control), conditions (Random delay/Sham), and electrodes (Cz/DET) did not result in significant differences in slow wave power (F<2.594, P>0.133) or theta power (F<2.877 and p>0.116 for all main effects and interactions) between stimulation conditions or groups (FIG. 5B). Power in the spindle band was as expected higher at Cz than the detection electrode (DET, main effect Electrode, F(1,12)=11.292, p=0.006, $\eta$2=0.124), and slightly lower during Sham than Random stimulation (main effect Condition, F(1,12)=4.819, p=0.049, $\eta$2=0.004; Electrode×Condition, (F(1,12)=8.760, p=0.012, $\eta$2=0.001, FIG. 4D). Intriguingly inspection of the spectra showed that the spindle peak was at a slower frequency in patients than in the controls (patients=11.69±0.15 Hz, controls=13.27±0.22 Hz; main effect Group, F(1,12)=14.53, p=0.002, $\eta$2=0.548). Moreover, independent of the group, in the Random delay condition, the spindle peak frequency was slightly faster than in the Sham condition (main effect Condition, F(1,12), p=0.018, $\eta$2=0.004, suggesting externally elicited spindles to be faster than spontaneously occurring spindles. Analyses of SO rates revealed more SOs after Random stimulation (F(1,12)=8.882, p=0.011). Spindle rates revealed a higher density at Cz than the detection electrode site (F(1,12)=9.17, p=0.010, $\eta$2=0.094, Electrode main effect).

Overall, the distinct differences in spindle activity between stimulation conditions as well as between the patient and healthy control groups, in the presence of rather comparable slow activity led the inventors to assume sleep spindles to be more relevant than SOs for conveying the suppressing effect of Radom delay stimulation on the patient's spike rates, and the inventors subsequently focused analyses on spindles. Moreover, because slow oscillatory activity is a sensitive measure of sleep depth, these measures being unaffected by Random delay in comparisons with the Sham control condition, excludes that effects of this stimulation spike rates were mediated by a nonspecific lightening of sleep.

Does the Effect of Acoustic Stimulation Result from a Competitive Relationship Between Sleep Spindles and IEDs?

Figure 6:
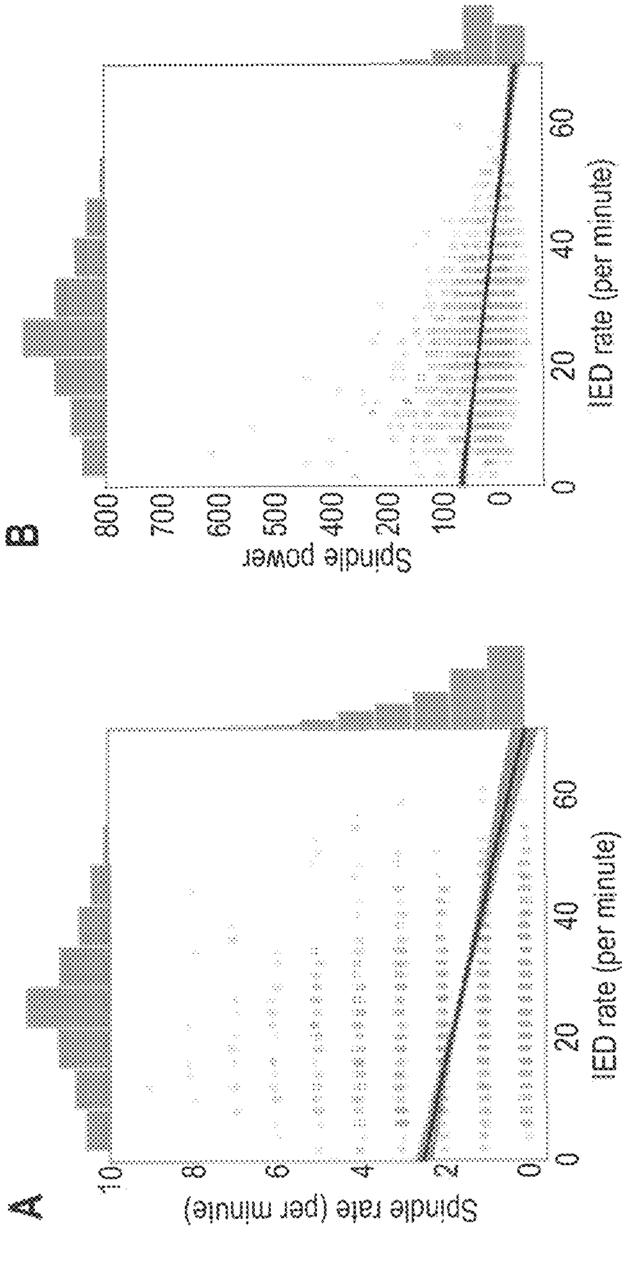
FIG. 6 IED rate is negatively correlated with spindle rate and power. Across all conditions, higher spike rates were associated with lower spindle power and rate, pointing to a competitive relationship between epileptic activity and sleep spindles. Each grey circle represents a single 30-s stimulation block, the regression line is shown in black±bootstrapped 95% confidence interval (both Pearson $r<-0.231$ and $p<2.019\times10^{-17}$). Rates are integers leading to largely overlapping data points. To increase clarity, values are slightly jittered along the y axis and marginal histograms illustrate the distribution of values across each axis.

Considering the partial overlap in the thalamo-cortical circuits mediating sleep spindles and IEDs, the inventors asked whether spindles might lower IEDs rates by occupying these networks and thereby preventing a simultaneous generation of IEDs. To test this, the inventors correlated the rate of IEDs with spindle power and spindle rates within 30-s stimulation blocks pooled across patients. This analysis revealed moderate but highly significant negative correlations for all stimulation conditions ($r<-0.231$ and $p<2.019\times10^{-17}$ for spindle power and spindle rate correlations across all conditions; all $r<-0.135$ and $p<0.023$, uncorrected, for correlations within individual conditions; values taken from detection electrode, FIG. 6) which is consistent with the hypothesis of a principal competitive relationship between pathological epileptic and physiological spindle activity.

Spikes and Tones Evoke Comparable Spindle Activity

Up to here, the inventors demonstrated an effect of acoustic random delay stimulation on the occurrence rate of IEDs. The inventors now assessed the activity associated with both spikes and tones and whether this activity was modulated by different stimulation conditions. FIG. 7A shows grand averages of time-frequency resolved event-related EEG responses to the IED for the Sham condition, the three peri-spike stimulation conditions, and the Random delay condition in the patient group (data from control group not shown). Visual inspection of IED-evoked changes in spectral power in the Sham condition (top row) shows that spikes are followed by a distinct increase in 10-18 Hz spindle power. The peri-spike stimulation conditions (rows 2-4) show a similar response, with the addition of characteristic auditory evoked power increases. In order to statistically dissociate the response to the tone, the inventors tested the peri-spike stimulation conditions against Sham. This resulted in significant differences with clusters spanning the spindle range and lower event-related frequencies. An increase in a similar frequency band emerged after auditory stimulation in the Random delay condition (bottom row), where spike-evoked activity is approximately averaged out. Overall, these analyses revealed that IEDs and tone invoked comparable increases including and most importantly in the spindle frequency range. Following the inventors' hypothesis of a competitive interaction between spindles and spikes, the inventors more closely compared the spike-evoked (Sham condition) and tone-evoked (Random delay condition) spindle responses for both the patients and control children (power estimates averaged between 10 and 18 Hz and from 0.4 to 1.2 s, FIG. 7B). In this analysis, healthy controls remained at baseline spindle activity in the Sham condition (due to missing spikes in these children) but distinctly increased spindle activity in response to the tones presented in the Random delay condition (Random delay vs. Sham, Holm-corrected $p=0.033$, $d=0.903$). By contrast, the patients showed spindle increases in response to both IEDs (Sham) and tones (Random delay) with a comparable magnitude of these responses (Random delay vs. Sham, Holm-corrected $p=1.00$; $p=0.019$, $eta^2=0.117$, for ANOVA Patient/Control×Sham/Random delay interaction.

Do Spike- and Tone-Evoked Responses Interact?

Figure 7:
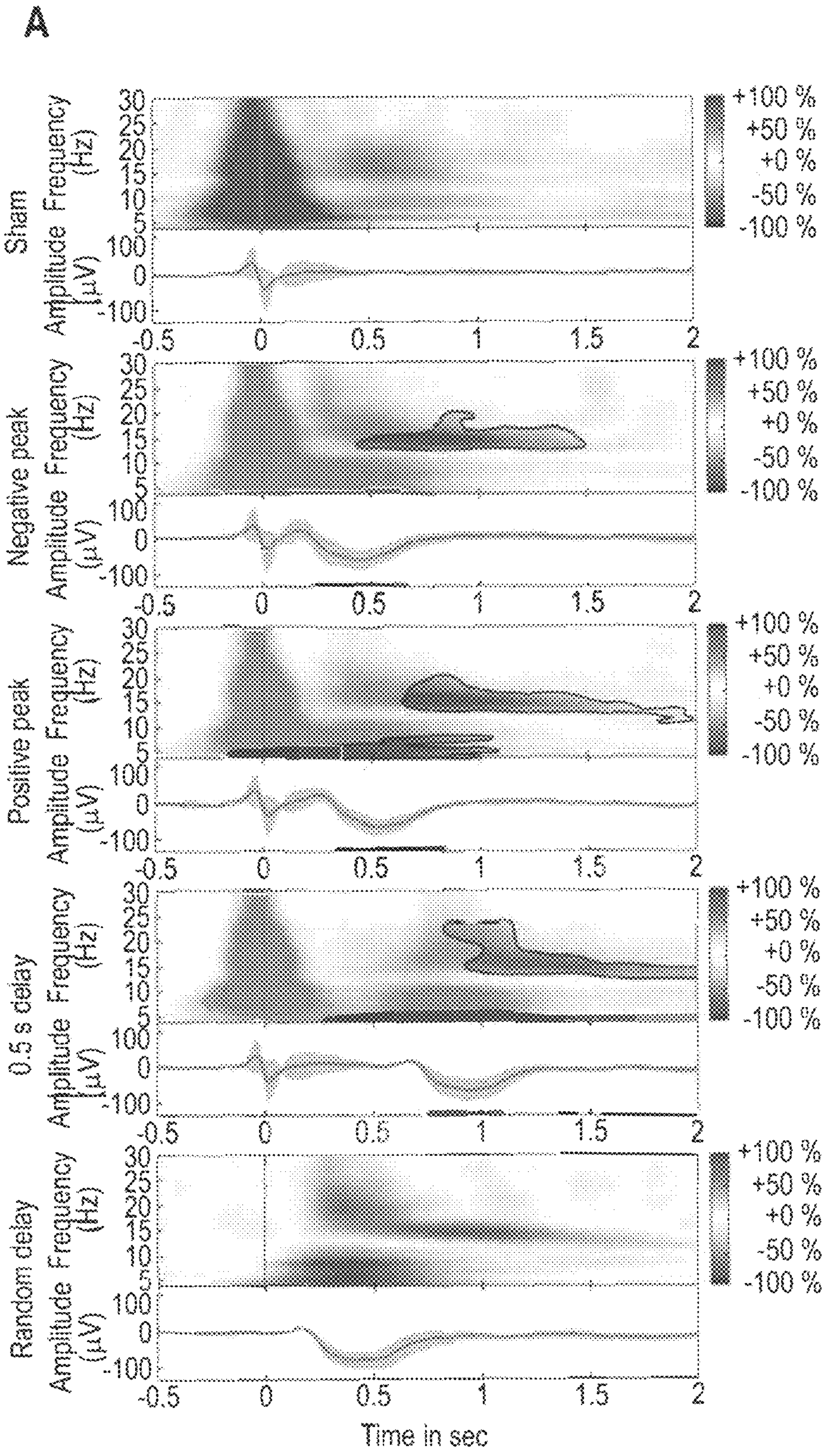
FIG. 7 Neural responses to IEDs and tones. A) Neuronal responses to IED-triggered acoustic stimulation in the patient group, aligned to detected IEDs (or tone in Random delay condition) at time 0. A) Each panel shows the time-frequency representation (top; colors denote power change relative to baseline −1.5 to −0.5 s before the IED negative peak) and time-domain representation (bottom; bands show 95% confidence interval) of the response. Responses in the Negative peak, Positive peak, and 0.5 s delay conditions were compared to Sham (power: black contours show significant clusters, non-significant areas are covered by a half-transparent mask; time-domain: horizontal bars show significant clusters, all cluster level $p<0.05$). B) Evoked spindle power (10-18 Hz, 0.4-1.2 s after IED negative peak, ±boot-strapped SEM), relative to baseline, extracted from time-frequency data in A). In patients (light grey), auditory stimulation triggered spindle responses of similar strength as those evoked by epileptic spikes (post-hoc test Random delay vs. Sham, Holm-corrected $p=1.00$). In contrast, in control subjects (dark grey), the Sham condition did not contain stimulation or spikes, leading to spindle power around baseline levels and significantly lower than for Random delay stimulation (Random delay vs. Sham, Holm-corrected $p=0.033$; ANOVA Patient/Control×Sham/Random delay, $p=0.019$). Stimulation-induced spindle power did not significantly differ across groups (Random delay patients vs. controls, Holm-corrected $p=1.00$). C) Evoked spindle power differed significantly across the stimulation conditions (light grey line, ANOVA Sham/Negative peak/Positive peak/0.5 s delay, main effect Condition, $p=0.007$). When subtracting the isolated auditory-evoked response of the Random delay condition (stimulation-aligned) before assessing spindle power, this difference vanished (dark grey, $p=0.752$).
Figure 7:
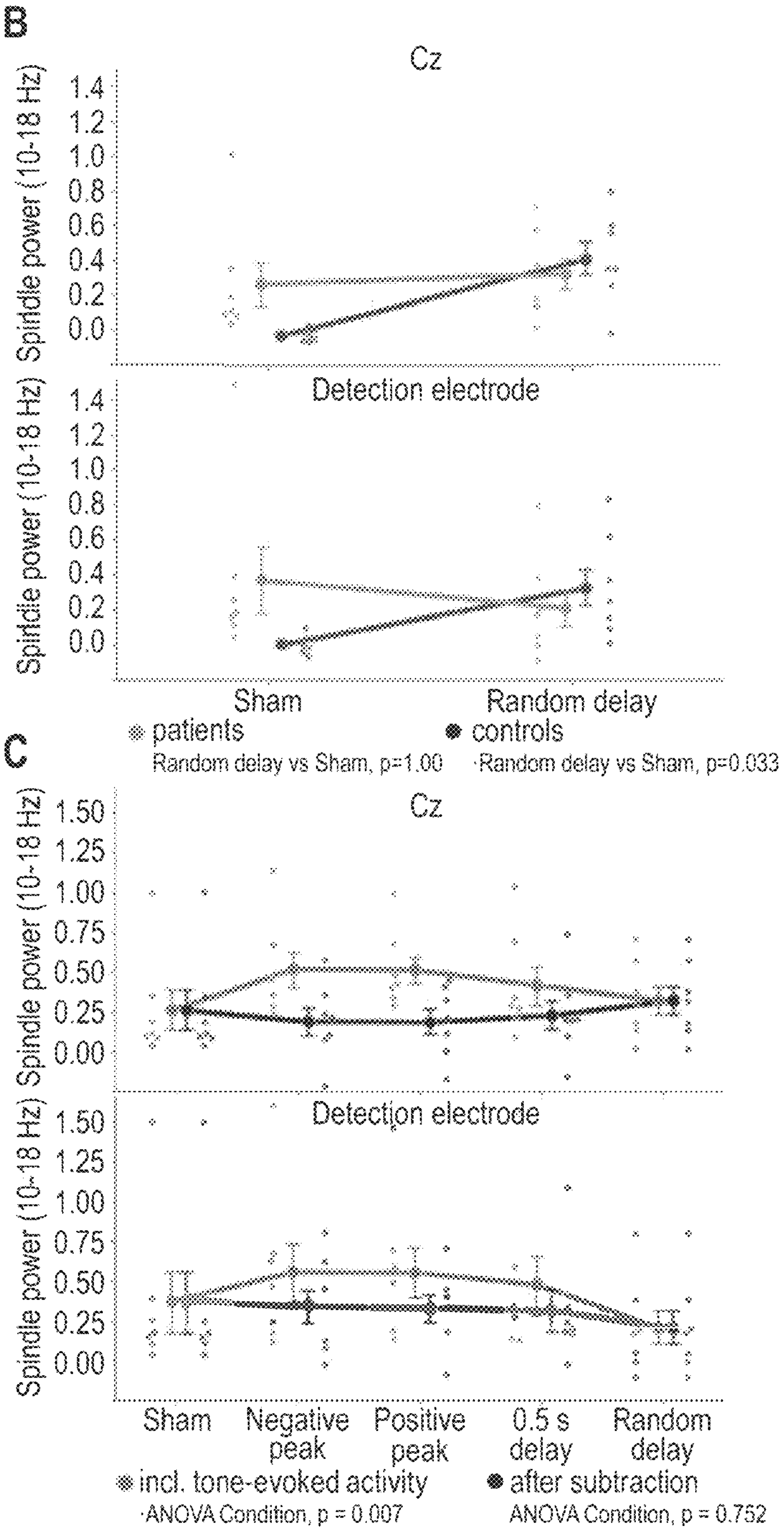

After demonstrating that IEDs and tones in isolation evoke comparable spindle responses, the inventors explored whether the hypothesized competitive relationship of IEDs and tones is expressed in an interference in their respective evoked activity. The inventors assumed that, when the thalamo-cortical network is occupied with generating a spike and associated spindle activity, auditory stimulation would result only in a dampened spindle response. According to the opposing null hypothesis, activity in the peri-spike stimulation conditions would be a mere superposition of spike- and tone-evoked activity. To discern these two scenarios, the inventors compared the spectral power response to the IED in the Sham condition (reflecting the pure response to the spike in the absence of any tone) with the response to the IED in the Negative peak, Positive peak, and 0.5 s delay stimulation conditions (FIG. 7 C, grey line). Spindle power was significantly different across these four conditions (main effect Condition $p=0.007$, $eta^2=0.052$; test performed excluding Random delay condition). As a next step, the inventors subtracted tone-evoked responses from the peri-spike stimulation conditions before extracting spindle power. For estimating the tone-evoked power responses, the inventors used the Random delay condition because in this condition, IED-evoked modulations are assumed to average out to zero, resulting in a pure auditory response. FIG. 7C (red line) shows that after subtracting tone-evoked power changes, spindle responses in the Negative peak, Positive peak and 0.5 s delay conditions do not differ anymore from those in the Sham condition (main effect Condition, $p=0.752$). These results suggest that spindle responses in the peri-spike stimulation conditions are the result of a mere superposition of responses evoked by spikes or tones in isolation, without strong mutual interactions. Therefore, the competitive effect of tone-evoked activity and IEDs does not extend to IED-associated spindle activity, making a contribution of the latter to IED suppression unlikely.

Figure 8:
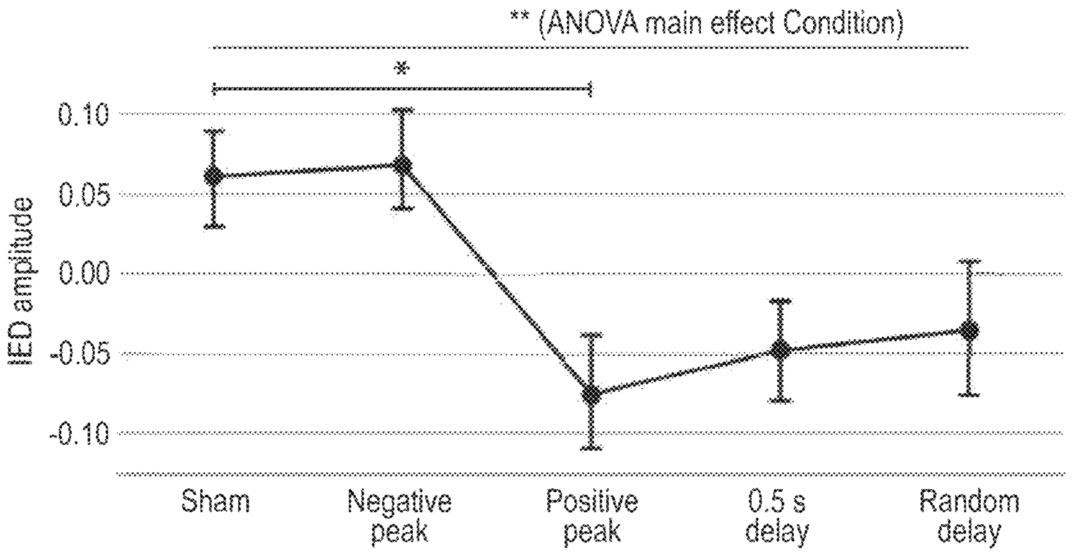
FIG. 8 Tones decreased the amplitude of immediately following IEDs. Amplitude of spikes following auditory stimulation or sham (0-1.5 s) were reduced in amplitude (ANOVA on pooled data, main effect Condition $p=0.002$). When compared to Sham, this reduction was significant for the Positive delay condition (Holm-corrected $p=0.021$; 0.5 s delay, $p=0.121$; Random delay, $p=0.250$). $^{*}p<0.05$; $^{**}p<0.01$.

A possible immediate interaction between tone- and IED-related activity may also manifest in the other direction, i.e., an effect of tones on the morphology of immediately following IEDs. Therefore, in a complementary analysis, the inventors focused on spikes that occurred within a 1.5-s interval following a tone stimulation (FIG. 8). Compared with respective spikes in the Sham condition, spike amplitudes in the 1.5-s post-stimulation interval were significantly altered ($F(4,4573)=4.274$, $p=0.002$, $\eta^2=0.004$). Post-hoc tests against Sham showed descriptive reductions in all except the Negative peak condition and reached significance for the Positive peak condition (Holm corrected $p=0.021$, $d=-0.138$). In summary, while the results do not demonstrate an immediate effect of spikes on the expression of tone-evoked activity, they show that tones reduced the amplitude of subsequent IEDs, if the stimulation is not administered right at its negative peak.

5. Discussion

The inventors show by experiments that auditory stimulation during NonREM sleep in children with Rolandic epilepsy or BECTS does suppress pathological interictal neural activity when timed mainly outside the close temporal proximity of IEDs. Across conditions, rate and power of spindles were negatively correlated with the rate of IEDs. The inventors hypothesize that this effect results from a stimulation-induced spindle refractoriness affecting subsequent IEDs that would have otherwise emerged from the same thalamocortical networks. Importantly, analysis of slow wave activity and slow oscillation events confirms that the effect of stimulation is not merely the result of lightened sleep. On the contrary, SO density was even slightly increased in the most effective Random delay condition, suggesting deeper sleep.

What could be the neurophysiological origin of a competitive relationship between sleep spindles and IEDs? Auditory stimulation induces cortical down states, which in turn lead to thalamic hyperpolarization, associated rebound bursting in thalamo-cortical cells, and thereby sleep spindles. The inventors propose a close relationship between these spindles and pathological IEDs as previous investigations have shown large overlaps in their thalamocortical origin and circuit-level mechanisms. The inventors' results extend these findings by showing that the peak spindle frequency is lower in patients than healthy controls, which may suggest that IEDs lead to pathological alterations of the same thalamocortical system that also generates spindles. Furthermore, sleep spindles show a refractory period of up to several seconds, resulting from intra-thalamic changes in excitability and refractory periods have also been shown for interictal spikes. Refractory periods may thus be shared by the two phenomena, such that spindles inhibit the occurrence of subsequent IEDs. This hypothesis would explain why IEDs and spindles are negatively correlated across conditions, while stimulation only suppressed IEDs when delivered mostly outside of epileptic discharges. Once an IED has triggered a thalamocortical refractory period, eliciting a spindle-associated refractory period in additional, spike-unaffected thalamocortical connections would remain without effect on the generation of further IEDs. However, when tones are applied mostly outside of ongoing epileptic discharges, they may capitalize on the negative spindle-IED relationship and suppress further discharges.

Similar to tones, also IEDs induce thalamic hyperpolarization, subsequent bursting rebound, and associated spindle oscillations. In the inventors' analyses, the spectral composition of these IED-induced spindles did not significantly differ from stimulation-induced spindles. The inventors further investigated whether an interaction of spindles triggered by IEDs and those triggered by tones could provide further insight into the origin of the demonstrated suppression effect. However, the inventors' analyses did not show a significant interaction of IED- and tone-induced activity. Subtracting auditory-evoked activity from the electrophysiological signal resulted in spindle levels comparable across sham and peri-spike stimulation conditions. IEDs as rather local phenomena may not affect global auditory processing to an extent discernible by the current study. Source reconstructing high-resolution electrophysiological recordings may allow investigating the respective effects within networks comparably affected by tone- and IED-induced spindles.

6. Conclusion

To summarize, the inventors present evidence for a therapeutic effect of auditory stimulation on interictal epileptiform discharges epilepsy patient, in particular in children with Rolandic epilepsy or RE-like centrotemporal spikes. As the underlying mechanism, the inventors propose a competitive mechanism of sleep spindles and IEDs, based on commonalities in their thalamocortical generation. Already 30 years ago, Mircea Steriade proposed that "[ . . . ] any pharmacological manipulation that would decrease or abolish the inhibitory efficacy of the [reticular] spindle pacemaker upon thalamo-cortical neurons [ . . . ] would also decrease the incidence of epileptic [spike wave] discharges" (Steriade, 1990). With this study, the inventors present first evidence that, as an alternative to pharmacological interventions, entirely non-invasive acoustic manipulation does have an equivalent effect.

Therefore, what is claimed is:

1. An apparatus for the treatment of an epilepsy-associated disorder in a living being, comprising, in an operatively linked manner:

an electrode set capable of obtaining an electroencephalogram (EEG) of the living being;

an audio output device capable of delivering an audio signal to the living being;

an analysis and control unit capable of:

(i) detecting interictal epileptic discharges (IED) in the EEG of the living being, and (ii) causing the audio output device to deliver the audio signal in time dependence of a detected IED, and wherein the analysis and control unit is configured to cause the audio output device to deliver the audio signal to the living being at a time delay after a detected IED, and the time delay is between 1 second to 3 seconds relative to a negative peak of the detected IED.

2. The apparatus of claim 1, wherein the audio signal comprises 1/f noise.

3. The apparatus of claim 1, wherein the analysis and control unit is configured to cause the audio output device to deliver the audio signal to the living being for a time period of 50 ms.

4. The apparatus of claim 1, wherein the analysis and control unit is configured to cause the audio output device to deliver the audio signal to the living being with a volume of 12 dB above an individual hearing threshold of the living being.

5. The apparatus of claim 1, wherein the analysis and control unit comprises a band-pass filter configured for detecting the IED in the EEG of the living being.

6. The apparatus of claim 5, wherein the band-pass filter comprises frequency limits of 20 and 150 Hz.

7. The apparatus of claim 1, wherein the analysis and control unit is configured to run a threshold method using an amplitude threshold for detecting the IED.

8. The apparatus of claim 1, wherein the electrode set comprises a detection electrode or a reference electrode.

9. The apparatus of claim 1, wherein the analysis and control unit is further capable of:

(iii) determining a non-rapid eye movement (NonREM) sleep phase of the living being.

10. The apparatus of claim 9, wherein the analysis and control unit capable of:

(ia) detecting IEDs in the EEG of the living being during the NonREM sleep phase, and (iia) causing the audio output device to deliver the audio signal in time dependence of a detected IED during the NonREM sleep phase.

11. The apparatus of claim 1, wherein the audio output device is a headphone.

12. The apparatus of claim 1, wherein the apparatus is configured for the treatment of an epilepsy-associated disorder in a living being which is or is suspected from suffering from any of: epilepsy, childhood epilepsy or Rolandic epilepsy.

13. A method for the treatment of an epilepsy-associated disorder in a living being, comprising the following steps:

(1) obtaining an electroencephalogram (EEG) of the living being;

(2) detecting interictal epileptiform discharges (IED) in the EEG of the living being, and (3) administering an audio signal to the living being in time dependence of a detected IED, and wherein the audio signal is administered to the living being at a time delay after a detected IED, and wherein the time delay is between 1 second to 3 seconds relative to a negative peak of the detected IED.

* * * * *